US011331452B2

(12) United States Patent
Guo et al.

(10) Patent No.: US 11,331,452 B2
(45) Date of Patent: May 17, 2022

(54) STEERABLE INTRAVASCULAR CATHETER WITH RELEASABLE LOCKING MECHANISM

(71) Applicant: St. Jude Medical, Cardiology Division, Inc., St. Paul, MN (US)

(72) Inventors: Xiaoping Guo, Eden Prairie, MN (US); David Hong, Minneapolis, MN (US); John J. Buysman, Minnetonka, MN (US); Steven N. Willard, Bloomington, MN (US); Ryan K. Buesseler, Bristow, VA (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 337 days.

(21) Appl. No.: 16/562,398

(22) Filed: Sep. 5, 2019

(65) Prior Publication Data

US 2020/0078559 A1    Mar. 12, 2020

Related U.S. Application Data

(60) Provisional application No. 62/729,923, filed on Sep. 11, 2018.

(51) Int. Cl.
| | | |
|---|---|---|
| *A61M 25/01* | (2006.01) | |
| *A61B 5/00* | (2006.01) | |
| *A61B 18/14* | (2006.01) | |
| *A61B 5/287* | (2021.01) | |
| *A61B 18/00* | (2006.01) | |

(52) U.S. Cl.
CPC ........ *A61M 25/0147* (2013.01); *A61B 5/287* (2021.01); *A61B 5/6852* (2013.01); *A61B 5/6858* (2013.01); *A61B 18/1492* (2013.01); *A61M 25/0113* (2013.01); *A61M 25/0136* (2013.01); *A61B 2018/00267* (2013.01); *A61B 2018/00577* (2013.01); *A61M 2025/015* (2013.01)

(58) Field of Classification Search
CPC .......... A61M 25/0133; A61M 25/0136; A61M 25/0147; A61M 2025/015
See application file for complete search history.

(56) References Cited

U.S. PATENT DOCUMENTS

| | | | |
|---|---|---|---|
| 6,233,476 B1 | 5/2001 | Strommer et al. | |
| 6,498,944 B1 | 12/2002 | Ben-Haim et al. | |
| 6,690,963 B2 | 2/2004 | Ben-Haim et al. | |
| 6,788,967 B2 | 9/2004 | Ben-Haim et al. | |
| 7,197,354 B2 | 3/2007 | Sobe | |
| 7,263,397 B2 | 8/2007 | Hauck et al. | |
| 7,386,339 B2 | 6/2008 | Strommer et al. | |
| 7,536,218 B2 | 5/2009 | Govari et al. | |
| 2016/0089126 A1* | 3/2016 | Guo ................. | A61M 25/0136 604/95.04 |

* cited by examiner

*Primary Examiner* — Brandy S Lee
*Assistant Examiner* — Hong-Van N Trinh
(74) *Attorney, Agent, or Firm* — Dykema Gossett PLLC

(57) ABSTRACT

Aspects of the present disclosure are directed to intravascular electrophysiology catheters including a catheter handle with a steering-wire locking mechanism.

19 Claims, 10 Drawing Sheets

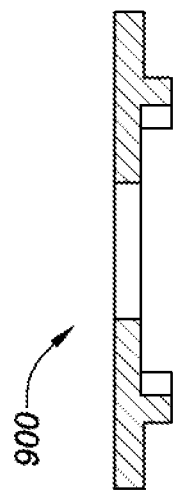
FIG. 9A
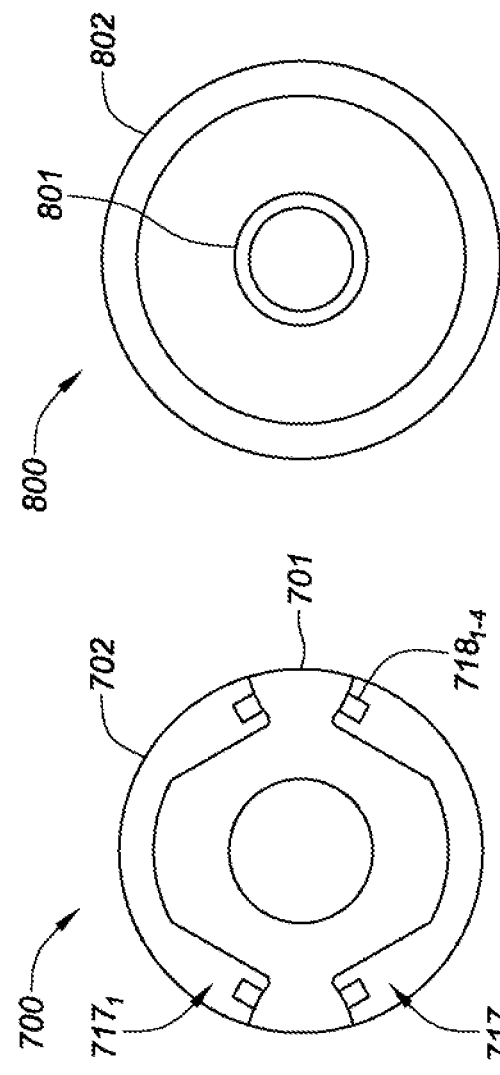
FIG. 9B
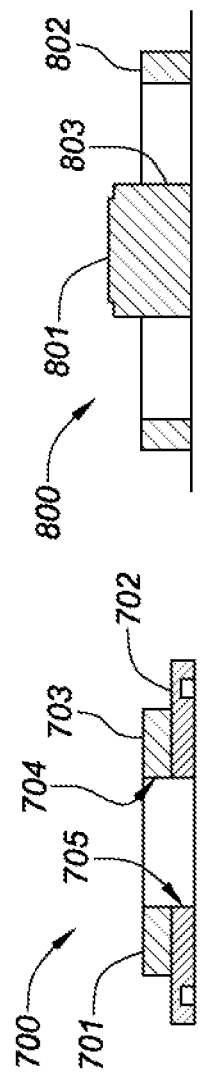
FIG. 8A
FIG. 8B
FIG. 7A
FIG. 7B

STEERABLE INTRAVASCULAR CATHETER WITH RELEASABLE LOCKING MECHANISM

CROSS-REFERENCE TO RELATED APPLICATION

This application claims the benefit of U.S. provisional application No. 62/729,923, filed 11 Sep. 2018, which is hereby incorporated by reference as though fully set forth herein.

BACKGROUND OF THE INVENTION a. Field of the Invention

The present disclosure relates to the design and manufacture of intravascular catheters; more specifically, catheter handles with releasable locking mechanisms.

b. Background Art

Electrophysiology catheters are used in a variety of diagnostic and/or therapeutic medical procedures to diagnose and/or correct conditions such as atrial arrhythmias, including for example, ectopic atrial tachycardia, atrial fibrillation, and atrial flutter. Arrhythmias can create a variety of conditions including irregular heart rates, loss of synchronous atrioventricular contractions and stasis of blood flow in a chamber of a heart which can lead to a variety of symptomatic and asymptomatic ailments and even death.

Medical procedures for diagnosing and/or treating arrhythmias may utilize an electrophysiology catheter deployed through a patient's vasculature to a patient's heart (or a chamber or vein thereof). A catheter handle including a steering mechanism may be utilized by a clinician to guide a distal portion or tip of catheter shaft through the patient's vasculature to a desired location for diagnosis and/or therapy application.

The electrophysiology catheter may have a conductive distal tip and/or one or more electrodes mounted at the deflectable distal portion of catheter shaft. The conductive tip and/or electrode(s) can be used for cardiac mapping or diagnosis, ablation and/or other therapeutic purposes, among others. Once the distal portion of catheter shaft is precisely positioned at an intended site of a patient's anatomy, treatment may include radio frequency (RF) ablation, cryoablation, laser ablation, chemical ablation, high-intensity focused ultrasound-based ablation, microwave ablation, etc. may be conducted. For therapeutic purposes, the electrophysiology catheter may impart ablative energy to cardiac tissue, for example, to create one or more lesions in the cardiac tissue and oftentimes a contiguous or linear, and transmural lesion. This lesion disrupts undesirable cardiac conductive or activation pathways and thereby limits, corrals, or prevents stray/errant conduction signals that can form the basis for arrhythmias. As readily apparent, such diagnosis and therapy delivery requires precise placement and retention of the distal portion of catheter shaft in the desired deflection configuration, such that the conductive tip and/or electrode(s) are precisely located at the target site within a patient's anatomy.

During an ablation therapy treatment, for example, a position/shape of a distal portion of the catheter must remain static for an extended period of time. The efficacy of the treatment may depend on the catheter's ability to maintain the position of the distal portion of the catheter in the desired deflection shape until the myocardial tissue in contact with the distal tip of the catheter has been completely ablated. To achieve the desired clinical outcome, aspects of the present disclosure are directed to catheter handle locking mechanisms which facilitate maintaining a deflected shape and position of the distal portion of the catheter shaft for a period of time.

BRIEF SUMMARY OF THE INVENTION

The instant disclosure relates to intravascular catheter apparatus (and systems); more specifically, aspects of the present disclosure are directed to electrophysiology catheters, including cardiac mapping and ablation catheters, for diagnosing and treating cardiac arrhythmias, for example. In particular, the instant disclosure relates to electrophysiology catheters that utilize catheter handles with a steering-wire locking mechanism for precise placement and retention of the distal portion of catheter shafts at a desired deflection shape within a patient's heart anatomy.

Aspects of the present disclosure are directed to a steering-wire locking system for deflecting a distal portion of a catheter shaft. The steering-wire locking system includes an outer race, an inner race, a plurality of rollers, and a plurality of compression springs. The inner race is co-axial with the outer race, and the outer race circumferentially extends around the inner race. The inner race includes one or more channels that extend into an outer perimeter of the inner race, and each channel houses a pair of compression springs and rollers. The plurality of rollers rotate within the race channels confined by an outer surface of the inner race and an inner surface of the outer race. The plurality of compression springs position the rollers in one of two positions within the race channels.

In some more specific embodiments of a steering-wire locking system for deflecting a distal portion of a catheter shaft, compression springs, in response to a clockwise rotation of the inner race, position a first roller of the plurality of rollers in a first position, and a second roller of the plurality of rollers in a second position. Further, in response to a counter-clockwise rotation of the inner race, the compression springs position the first roller of the plurality of rollers in the second position, and the second roller of the plurality of rollers in the first position. In yet further embodiments, at the first position, the roller is in contact with a distal end of the paired spring, within one of the channels, and the spring is fully extended. As a result, the roller exhibits a limited frictional coefficient with the inner and outer races. At the second position, the roller is in contact with a distal end of the paired spring, at least partially compressing the spring. As a result, the roller exhibits an enhanced frictional coefficient with the inner and outer races.

The foregoing and other aspects, features, details, utilities, and advantages of the present disclosure will be apparent from reading the following description and claims, and from reviewing the accompanying drawings.

BRIEF DESCRIPTION OF THE DRAWINGS

Various example embodiments may be more completely understood in consideration of the following detailed description in connection with the accompanying drawings, in which:

FIG. 7A is a cross-sectional front view of an inner race of a steering-wire locking mechanism, consistent with various embodiments of the present disclosure;

FIG. 7B is a top view of the inner race of FIG. 7A, consistent with various embodiments of the present disclosure;

FIG. 8A is a cross-sectional front view of an outer race of a steering-wire locking mechanism, consistent with various embodiments of the present disclosure;

FIG. 8B is a top view of the outer race of FIG. 8A, consistent with various embodiments of the present disclosure;

FIG. 9A is a cross-sectional front view of an actuating disc of a steering-wire locking mechanism, consistent with various embodiments of the present disclosure;

FIG. 9B is a top view of the actuating disc of FIG. 9A, consistent with various embodiments of the present disclosure;

Figure 1:
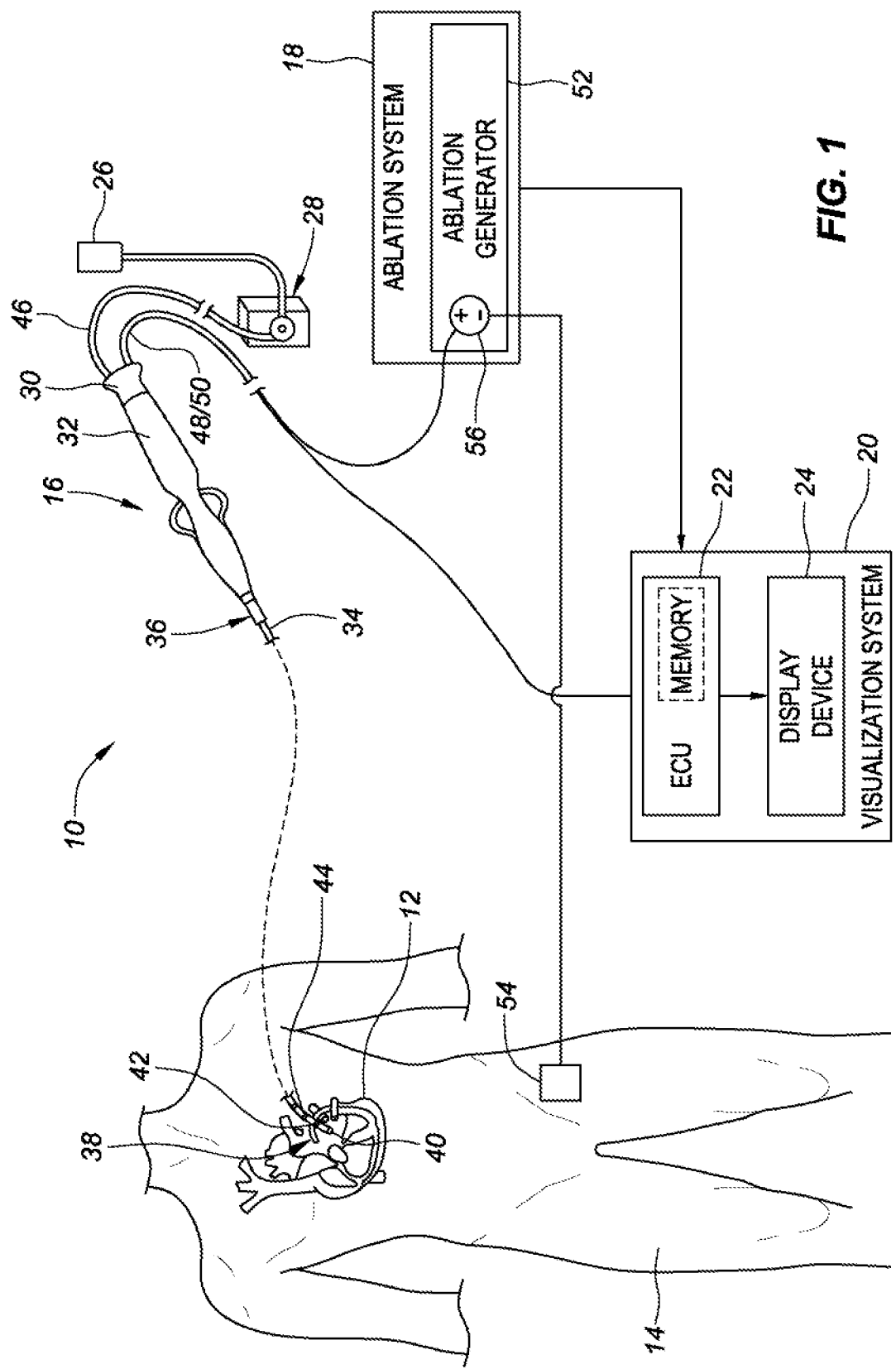
FIG. 1 is a diagrammatic view of a system for performing diagnostic and/or therapeutic functions on cardiac tissue, consistent with various embodiments of the present disclosure.

While various embodiments discussed herein are amenable to modifications and alternative forms, aspects thereof have been shown by way of example in the drawings and will be described in detail. It should be understood, however, that the intention is not to limit the invention to the particular embodiments described. On the contrary, the intention is to cover all modifications, equivalents, and alternatives falling within the scope of the disclosure including aspects defined in the claims. In addition, the term "example" as used throughout this application is only by way of illustration, and not limitation.

DETAILED DESCRIPTION OF EMBODIMENTS OF THE INVENTION

The instant disclosure relates to intravascular catheter apparatus (and systems); more specifically, aspects of the present disclosure are directed to a catheter handle of an intravascular catheter with a steering-wire locking mechanism, for example. In particular, the instant disclosure relates to a steering-wire locking mechanism which automatically locks the steering wire after a clinician's actuation of the catheter handle.

While various embodiments of the present disclosure are directed to electrophysiology (EP) mapping catheters, ablation catheters, and combinations thereof. Aspects of the present disclosure may further be applied to basket catheters, planar array catheters, among other catheters which may benefit from a steering-wire locking mechanism, in accordance with the present disclosure.

Aspects of the present disclosure are further directed to both uni- and bi-directionally deflectable intravascular catheters which facilitate varying levels of steering capability through a patient's vasculature. A bi-directionally deflectable catheter or introducer commonly used for cardiac mapping and ablation procedures typically has one or two steering wires (or otherwise commonly known as "pull wires"). To achieve bi-directional deflections via the activation of the steering wire(s), a catheter utilizes an actuator at a proximate end of catheter shaft, typically integrated into a catheter handle. For desirable steering characteristics, the actuator may exert a pull force on one steering wire which causes the deflection of the distal portion or tip (in one of the bilateral directions) within the deflecting plane passing through the longitudinal axes of the catheter shaft, while the other steering wire, if applicable, is passive or free of tension (or pull force). Aspects of the present disclosure are further directed to maintaining the deflected shape of the distal portion of catheter shaft by locking the activated steering wire that is in tension, until a further steering input is received by a clinician.

There are two commonly-used types of uni- and bi-directional actuators for various deflectable catheters for activating a steering wire: axial rotation and lateral rotation. The axial rotation actuator may utilize a lead screw-nut mechanism with self-locking features. The actuator is axially fixed with the nut. The actuator, accessible by a clinician, may be rotated to enact the deflection of the distal portion of catheter shaft. The rotational actuator transforms a clockwise (or counterclockwise) rotation of the actuator into the forward (or backward) axial motion of a steering wire of the deflectable catheter or steerable introducer. For bi-directional deflections of the catheter, the nut may include two continuous grooves helically-threaded on its inner cylindrical surface in opposite directions. These two grooves are mated with two respective half-screws (parallel with the same helical angles and pitches). When rotating the nut about the axis of the actuator body, the two half-screws, which are coupled to the two steering wires, move axially in opposite directions, facilitating deflection of the distal tip portion of the catheters/introducers in one of the two directions. Such axial rotational actuators for bidirectional deflectable catheters may have helical angles based on the static frictional coefficient for the materials used for the lead screws and nut (e.g., polymeric material). Accordingly, the axial rotational actuator may self-lock upon the release of the actuating forces on the actuator or nut in either direction (clockwise or counterclockwise). One example of bidirectional deflectable catheters with an axial rotational actuator is the Livewire™ family of mapping and ablation catheters manufactured by Abbott Laboratories Incorporated.

Intravascular catheters with lateral rotational actuators are also readily available, including Safire™, Reflection™, and Flexability™, all from Abbott Laboratories Inc., as well as EPstar Snake from J-Cath, Thermocool™ from Biosense Webster, etc. These various catheters utilize bilateral rotation of the actuator to achieve axial motion of the steering wire along the catheter shaft. For example, a sliding linkage, a rack-gear mechanism, and wrapping flexible cords made of high strength polymer fiber strands, among other techniques may be utilized to achieve the desired distal deflection of catheter shaft. Existing bidirectional deflectable catheters including a lateral actuator utilize a separate mechanism to facilitate locking a position of the active or activated steering wires. For example, a typical lock mechanism for a lateral actuator may utilize a frictional disc sandwiched between the lateral actuator and a stationary element (e.g., catheter handle body). Tightening the frictional disc against the moving and stationary elements via a tightening knob, for example, screwed into the stationary element generates high normal forces which lead to high frictional forces. The high friction limits potential bilateral rotation of the steering actuator in response to either clinician input, or disturbances from the distal portion of the catheter shaft within the beating heart, preventing movement of the active steering wire relative to the locking mechanism. To adjust a deflection of the distal portion of catheter shaft, a clinician must input a driving torque on the actuator which overcomes a static frictional torque arising from the tightened frictional disc or release the tightening knob. When in a locked configuration, static frictional torque arising from the frictional disc prevents the actuator from rotation upon release of the driving torque or by system disturbance (e.g., an external force exerted on the distal catheter portion including the distal tip). This approach to a lockable steering actuator is used in various commercially available catheter products, as identified above. However, such lateral actuator locking mechanisms may suffer from one or more drawbacks. For example, the locking may not be preset, and in-field adjustment of the lock via the tightening knob is compulsory. Further, the locking mechanism may not necessarily be pre-set from the factory when the locking mechanism includes polymeric materials (e.g., pivot base, frictional component and tightening knob). Polymeric materials are not suited for constant high loading which may cause viscoelastic or relaxation behaviors, resulting in the decay of the preset frictional forces (or torques). However, the use of metallic materials, alone or in conjunction with polymeric materials, may raise cost, as well as assembly complexity. Accordingly, various embodiments of the present disclosure are directed to a steering-wire locking mechanism with improved functionality, manufacturability, and cost.

Various cardiac ablation catheters, consistent with the present disclosure, facilitate the steerable delivery of the catheter through a patient's vasculature and the desirable distal deflection of the catheter shaft to achieve desired positioning of the catheter tip or distal electrodes within a patient's cardiovascular anatomy. The distal deflection of the catheter shaft is often achieved using a steering wire (also referred to herein as a steering wire) which is attached to a steering mechanism in the catheter handle. In response to an actuation by a clinician, a steering wire (or pull wire) moves relative to the catheter shaft to achieve distal deflection. Aspects of the present disclosure are directed to minimizing the force required to affect steering, and in the absence of a steering input by the clinician, locking the active or activated steering wire to securely maintain the distally deflected shape of the catheter shaft. In some specific embodiments, the active steering wire is locked in its activated position when no external force by the clinician is applied to the steering mechanism. In response to a clinician's new actuation of the steering mechanism, the active steering wire is released, allowing the clinician to deflect the tip to the new desired position with minimal force application.

One embodiment of a steering-wire locking mechanism, consistent with the present disclosure, utilizes two askew arms to lock a sliding piston in place when no force is applied to the mechanism. The lock is activated when the askew arms are in direct contact with a high-friction wall which provides the locking force. When force is applied to an unlock component of the mechanism, it pulls one arm away from the high-friction wall and allows a piston coupled to the steering wire to slide in a direction. One benefit of the present embodiment is a clinician's ability to slide the unlock component and adjust a distally deflected shape of catheter shaft at will, while the absence of an applied force on the locking mechanism maintains a position of the steering wire and accordingly the deflected shape for the distal portion of catheter shaft with inherent capacity of locking the active steering wire. As a result, the steering and deflecting operations of the catheter by the clinician are simplified.

In another example embodiment of a steering-wire locking mechanism, the mechanism may include wedges and springs to lock the steering wire (or pull wire) in place relative to a catheter shaft when no force is applied to a steering actuator of the catheter handle. When force is applied to the steering actuator, the wedges spread apart, releasing pressure on the locks and allowing axial movement of the locking mechanism relative to the catheter shaft. At least two configurations of such an embodiment are readily envisioned. The first embodiment contains four wedges, or a quad-wedge arrangement, and the second embodiment utilizes two-wedges. Aspects of the present embodiments benefit from a reduced pressure required to overcome the friction of the locking mechanism, when engaged. The locking mechanism engages the steering wire to prevent undesirable actuation, maintains a clinician's deflection input on the steering actuator, and releases the steering wire in response to a clinician's actuation of the steering actuator—greatly reducing complexity of use. Such embodiments are disclosed in more detail in reference to FIGS. 3A-4B.

Referring now to the drawings wherein like reference numerals are used to identify identical components in the various views, FIG. 1 illustrates one example embodiment of a system 10 for performing one or more diagnostic and/or therapeutic functions in association with cardiac muscle 12 within a human body 14. It should be understood, however, that the system 10 may find application in connection with the ablation/diagnostics of a variety of other tissues within human and non-human bodies.

The system 10 may include a medical device (such as, for example, an electrophysiology catheter 16), an ablation system 18, and/or a system 20 for the visualization, navigation, and/or mapping of internal body structures. The system 20 may include, for example and without limitation, an electronic control unit (ECU) 22 and a display device 24. Alternatively, the ECU 22 and/or the display 24 may be separate and distinct from, but electrically connected to and configured for communication with, the system 20.

With continued reference to FIG. 1, the catheter 16 can be provided for examination, diagnosis, and/or treatment of internal body tissues such as within a cardiac muscle 12. In an example embodiment, the electrophysiology catheter 16 is a diagnostic catheter, such as a cardiac mapping catheter that may include a plurality of electrodes configured to monitor one or more electrical signals transmitted throughout the adjacent cardiac tissue. For example, electrophysiology catheter 16 may comprise a linear ablation catheter. The ablation catheter may be irrigated in an embodiment such that the catheter 16 may further comprise an inner fluid delivery tubing that may include at least one fluid delivery port. In the present embodiment, wherein the catheter 16 is an irrigated catheter, the catheter 16 can be connected to a fluid source 26 providing a biocompatible fluid such as saline, or a medicament, through a pump 28 (which may comprise, for example, a fixed-flow-rate roller pump or variable volume syringe pump with a gravity feed supply from the fluid source 26, as shown) for irrigation. It should be understood, however, that catheter 16 is not limited to an ablation catheter and is not limited to an irrigated catheter. Rather, in other embodiments, the catheter 16 may comprise an ablation catheter (e.g., radio frequency (RF), cryoablation, ultrasound, etc.), a mapping catheter, or a combination thereof. The catheter may be configured with or without irrigation.

In one example embodiment where the catheter comprises an ablation catheter, the catheter 16 is electrically connected to the ablation system 18 to allow for the delivery of ablative energy, or the like. The catheter 16 may include a cable connector or interface 30, a handle 32, a shaft 34 having a proximal end 36 and a distal end 38, and one or more electrodes 40, 42 mounted in or on the shaft 34 of the distal portion of catheter 16. In an example embodiment, the electrodes 40, 42 are disposed at or near the distal end portion 38 of the shaft 34, with the electrode(s) 40 comprising an ablation electrode disposed at the extreme distal end portion 38 of the shaft 34 (i.e., tip electrode 40), and the electrode(s) 42 comprising a spot electrode used, for example, with the visualization, navigation, and EP mapping system 20. Spot electrode(s) 42 can be configured to provide a signal indicative of both a position and orientation of at least a portion of the catheter 16. The catheter 16 may further include other conventional components such as, for example and without limitation, a temperature sensor (or sensors) 44, additional electrodes, and corresponding conductors.

The connector 30 provides mechanical, fluid, and electrical connection(s) for cables 46, 48, 50 extending from the pump 28, the ablation system 18, and the visualization, navigation, and/or mapping system 20. The connector 30 is conventional in the art and is disposed at the proximal end 36 of the catheter 16.

The handle 32 provides a location for the clinician to hold the catheter 16 and may further provide means for steering or guiding the shaft 34 within the body 14 as known in the art. Catheter handles are generally conventional in the art and it will be understood that the construction of the handle 32 may vary. However, various embodiments of the present disclosure are directed to catheter handles which integrate an improved locking mechanism into a steering actuator. The improved locking mechanism facilitates automatic locking of the steering actuator in the absence of a clinician input on the actuator.

The shaft 34 is an elongate, tubular, flexible member configured for movement within the body 14. The shaft 34 supports, for example and without limitation, one or more electrodes (e.g., electrodes 40, 42), associated conductors, and possibly additional electronics used for signal processing, visualization, localization, and/or conditioning. The shaft 34 may also permit transport, delivery and/or removal of fluids (including irrigation fluids, medicaments, and bodily fluids, etc.), medicines, and/or surgical tools or instruments. The shaft 34 can include one or more lumens configured to house and/or transport electrical conductors, fluids, or surgical tools. The shaft 34 can be introduced into a blood vessel or other structure within the body 14 through a conventional introducer. The shaft 34 is then steered or guided through the body 14 to a desired location such as the tissue 12 with steering wires (or pull wires) or other means known in the art.

As generally illustrated in FIG. 1, an ablation system 18 can be comprised of, for example, an ablation generator 52 and one or more ablation patch electrodes 54. The ablation generator 52 generates, delivers, and controls ablation energy (e.g., radio-frequency) output by the ablation catheter 16 and the tip electrode 40 thereof, in particular. The generator 52 is conventional in the art and may comprise a commercially available unit sold under the model Ampere Cardiac Ablation Generator, available from Abbott Medical Systems. In one embodiment, the generator 52 may include an RF ablation signal source 56 configured to generate an ablation signal that is output across a pair of source connectors: a positive polarity connector SOURCE (+), which electrically connects to the tip electrode 40 of the catheter 16; and a negative polarity connector SOURCE (−), can be electrically connected to one or more of the patch electrodes 54. It should be understood that the term connectors as used herein does not imply a particular type of physical interface mechanism but is rather broadly contemplated to represent one or more electrical nodes (including multiplexed and de-multiplexed nodes). The source 56 is configured to generate a signal at a predetermined frequency in accordance with one or more user specified control parameters (e.g., power, time, etc.) and under the control of various feedback sensing and control circuitry. The source 56 may generate a signal, for example, with a frequency of about 450 kHz or greater for RF energy. The generator 52 may also monitor various parameters associated with the ablation procedure including, for example, impedance, the temperature at the distal tip of the catheter, applied ablation energy, power, force, proximity, and the position of the catheter, and provide feedback to the clinician or another component within the system 10 regarding these parameters.

The visualization, navigation, and/or EP mapping system 20 with which the electrodes 42 can be used may comprise an electric field-based system, such as, for example, ENSITE NAVX (aka EnSite Classic as well as newer versions of the EnSite system, denoted as ENSITE VELOCITY) and commercially available from Abbott Laboratories Inc. and as generally shown with reference to U.S. Pat. No. 7,263,397 titled "Method and Apparatus for Catheter Navigation and Location and Mapping in the Heart," the entire disclosure of which is incorporated herein by reference. In accordance with an electric field-based system, the positioning electrode(s) 42 can be configured to be responsive to an electric field transmitted within the body of the patient. The electrode(s) 42 can be used to sense an impedance at a particular location and transmit a representative signal to an external computer or processor. In other embodiments, however, the visualization, navigation, and/or mapping system may comprise other types of systems, such as, for example and without limitation: a magnetic field-based system such as the CARTO System available from Biosense Webster, and as generally shown with reference to one or more of U.S. Pat. No. 6,498,944 entitled "Intrabody Measurement," U.S. Pat. No. 6,788,967 entitled "Medical Diagnosis, Treatment and Imaging Systems," and U.S. Pat. No. 6,690,963 entitled "System and Method for Determining the Location and Orientation of an Invasive Medical Instrument," the entire disclosures of which are incorporated herein by reference, or the gMPS system from MediGuide Ltd. of Haifa, Israel (now owned by Abbott Laboratories Inc.), and as generally shown with reference to one or more of U.S. Pat. No. 6,233,476 entitled "Medical Positioning System," U.S. Pat. No. 7,197,354 entitled "System for Determining the Position and Orientation of a Catheter," and U.S. Pat. No. 7,386,339 entitled "Medical Imaging and Navigation System," the entire disclosures of which are incorporated herein by reference. In accordance with a magnetic field-based system, the electrode(s) 42 can be configured to be responsive to a magnetic field transmitted through the body of the patient. The electrode(s) 42 can be used to sense the strength of the field at a particular location and transmit a representative signal to an external computer or processor. The electrode(s) 42 may comprise one or more metallic coils located on or within the catheter 16 in a magnetic field-based system. Alternatively, a combination electric field-based and magnetic field-based system such as the CARTO 3 System also available from Biosense Webster, and as generally shown with reference to U.S. Pat. No. 7,536,218 entitled "Hybrid Magnetic-Based and Impedance-Based Position Sensing," the entire disclosure of which is incorporated herein by reference, may be used. In accordance with a combination electric field-based and magnetic field-based system, the electrodes 42 may comprise both one or more impedance-based electrodes and one or more magnetic coils. Commonly available fluoroscopic, computed tomography (CT), and magnetic resonance imaging (MRI)-based systems can also be used to facilitate visualization and navigation.

Figure 2:
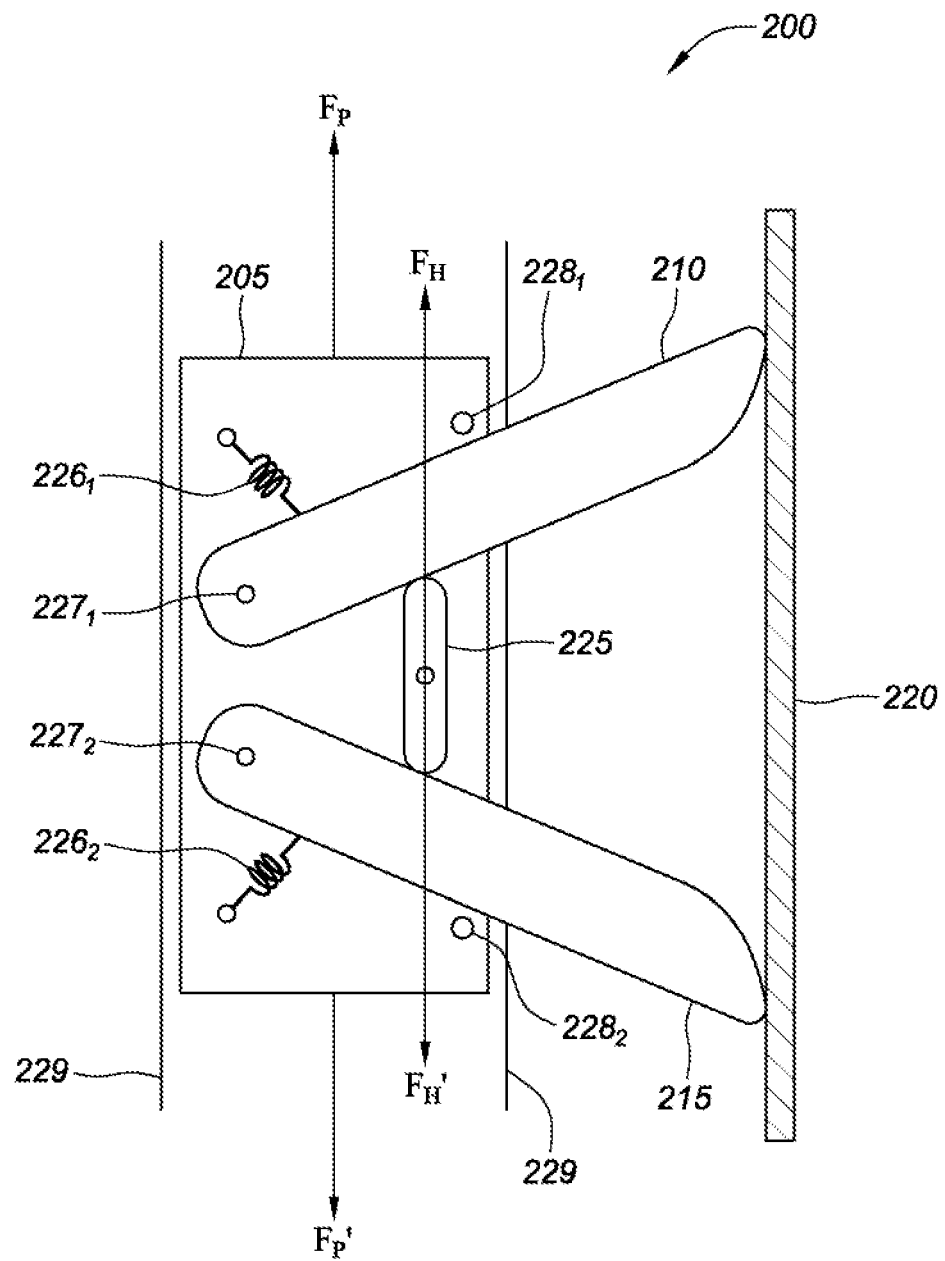
FIG. 2 is a diagrammatic top view of a steering-wire locking mechanism, consistent with various embodiments of the present disclosure.

FIG. 2 is a diagrammatic top view of a steering-wire locking mechanism 200, consistent with various embodiments of the present disclosure. The steering-wire locking mechanism utilizes askew arms 210 and 215 to lock a sliding piston 205 in place when no force is applied to an actuator (or unlock component) 225. The locking mechanism is activated when the arms 210 and 215 are in direct contact with a high-friction wall 220, thereby providing the locking force. The arms are biased into contact with the high-friction wall via compression springs $226_{1\text{-}2}$. When an actuating force ($F_H$ or $F_{H'}$) is applied to the actuator 225 in direction of actuation, one (active) arm is pulled away from the high-friction wall 220 and the piston is allowed to slide along the direction of actuation, with the other (passive) arm still dragging against the high friction wall 220.

One benefit of the present embodiment is a clinician's ability to slide the actuator 225 and simultaneously unlock and change the deflected distal shape of catheter shaft via the steering wire which is coupled to the piston 205. The absence of clinician actuation of the actuator 225 maintains a position of the steering wire by locking the piston in place relative to piston-sliding track 229 and high friction wall 220. Accordingly, the deflected distal shape of the catheter shaft is locked in place. The resulting embodiment simplifies operation of a catheter handle with integrated steering-wire lock.

When actuator 225 is static (e.g., not receiving a clinician input), compression springs $226_{1\text{-}2}$ push the arms 210 and 215 into the high friction wall 220, locking the piston 205 axially relative to piston-sliding track 229 and high friction wall 220. When pull force $F_P$ (or $F_{P'}$) from the steering wire is applied to the piston 205 (e.g., a steering wire coupled to the piston), the arm on the leading side of the piston, relative to the pull force $F_P$ (or $F_{P'}$), is locked against the high friction wall 220. This is because the actuator 225, in its neutral position, prevents rotation of the arms away from the high friction wall 220. For example, pull force, $F_P$, on the piston 205 exerts a clockwise moment on the upper side of arm 210. This exerted moment is in dynamic balance with the counterclockwise moment on the upper side of the same arm due to the compressive force from compression spring $226_1$. As a result, arm 210 and piston 205 are locked in position as arm 210 maintains its direct contact against high frictional wall 220.

Similar to the example presented above, pull force $F_{P'}$ on the piston 205 along another direction, when an actuation force $F_{H'}$ is absent, would not result in the axial motion of piston 205 relative to piston-sliding track 229 and high friction wall 220.

When an actuation force, $F_H$ or $F_{H'}$, is applied to actuator 225, the active arm in the direction of the actuation force is pushed away from high friction wall 220, thereby unlocking the piston. The other passive arm may still maintain contact with the high friction surface, but does not prevent the piston from sliding in the direction of the actuation force. As the present embodiment automatically locks the piston when no actuation is applied to actuator 225, and unlocks when an actuation force is applied to the actuator, the actuation force required to move the piston relative to the wall may be reduced.

The steering-wire locking mechanism 200 of FIG. 2 locks piston 205 in both directions when no actuation force ($F_H$ or $F_{H'}$) is applied to actuator 225. The compression springs $226_{1\text{-}2}$ cause arms 210 and 215 to be in direct contact with high-friction wall 220. As a result, the piston cannot slide axially (along piston-sliding track 229).

When upward actuation force $F_H$ is applied to actuator 225, the actuator pushes the askew, active arm 210 counterclockwise by overcoming the resistance from compression spring $226_1$ coupled to the arm such that the axial motion of piston 205 is unlocked. At the same time, the force ($F_H$) is transmitted to the piston 205, pushing piston 205 moves axially. The other askew, passive arm 215 may maintain contact with high-friction wall 220, due to compression spring $226_2$ coupled to the arm. However, the passive arm 215 is not locked due to its askew orientation relative to the wall, but may be dragged along with the sliding piston by the actuation force ($F_H$). When force $F_H$ is released, force $F_P$ (arising from a steering wire in tension) may be imposed on piston 205, while piston 205 is automatically locked in position by the arm 215 per the above discussion.

The locking mechanism 200 may work similarly if downward actuation force, $F_{H'}$, is applied since the system is symmetric along a horizontal axis.

The askew arms 210 and 215, respectively, rotate about their pivots $227_{1\text{-}2}$, compression springs $226_{1\text{-}2}$ provide a compression force that facilitates contact between the arms and high friction wall 220 (absent an actuation of actuator 225). Stops $228_{1\text{-}2}$ minimize rotational motion of the arms in response to the actuation of the actuator, and to transmit the longitudinal force from the actuation to piston 205 more efficiently than via the springs $226_{1\text{-}2}$ alone.

Figure 3A:
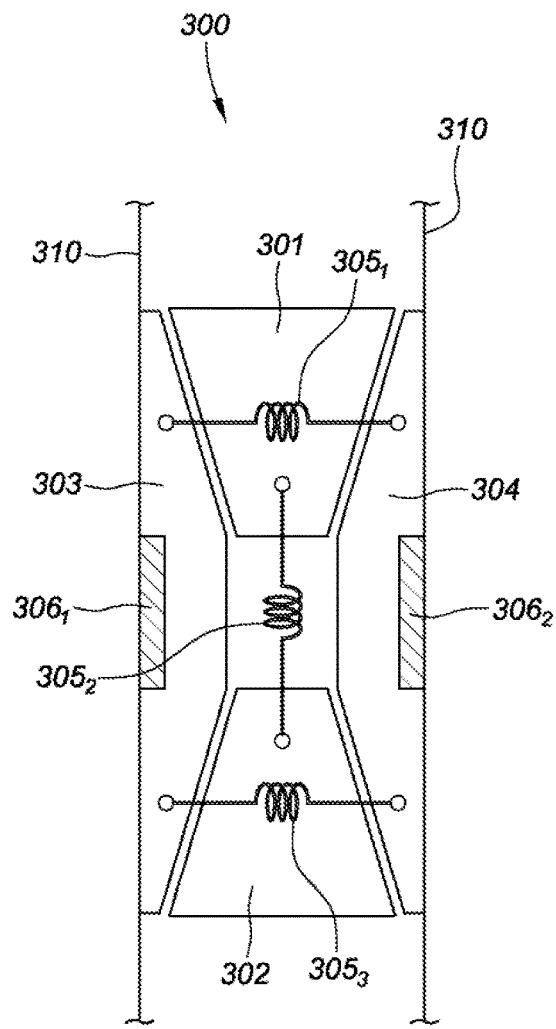
FIG. 3A is a diagrammatic, cross-sectional side view of a steering-wire locking mechanism in a locked configuration, consistent with various embodiments of the present disclosure.

FIG. 3A is a diagrammatic, cross-sectional side view of a steering-wire locking mechanism 300 in a locked configuration, consistent with various embodiments of the present disclosure. As shown in FIG. 3A, steering-wire locking mechanism 300 includes four wedges 301-304. The upward and downward wedges, 301 and 302, respectively, attach to an actuator on a catheter handle that the clinician actuates to deflect a distal portion of catheter shaft via steering wire(s) coupled to the mechanism. One or more steering wires may be coupled to the mechanism at one of the wedges. For example, side wedges 303 and 304 may be coupled to the steering wire(s) (or pull wires) which are used to deflect a distal portion of the catheter in response to an actuation by the clinician.

Springs $305_{1-3}$ couple wedges 301-304 together. Absent an actuation force, spring $305_2$ extends side wedges 303 and 304 laterally into contact with wall 310. The contact between the side wedges and the wall locks the locking mechanism 300 into place, and prevents axial motion of the steering wires coupled thereto. To further increase friction between the side wedges and the wall, some embodiments of the present disclosure may include high frictional coefficient regions $306_{1-2}$, which further facilitate a locked configuration of the locking mechanism 300 in response to elevated forces on the catheter shaft (which is translated back to the locking mechanism via the steering wires). Moreover, as discussed in reference to FIG. 3B, positioning the high frictional coefficient regions $306_{1-2}$ in an intermediate portion of the side wedges 303 and 304 facilitates improved sliding of the mechanism when in an unlocked configuration. This improved sliding is due to contact between the side wedges and wall 310 only at low-frictional coefficient regions of the side wedges.

Figure 3B:
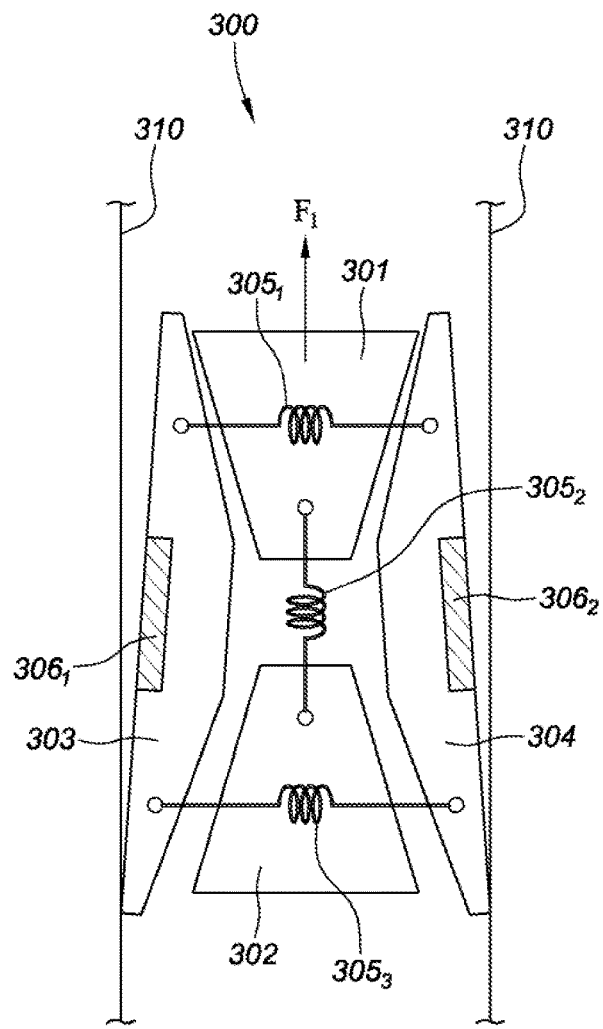
FIG. 3B is a diagrammatic, cross-sectional side view of the steering-wire locking mechanism of FIG. 3A in an unlocked configuration, consistent with various embodiments of the present disclosure.

FIG. 3B is a diagrammatic, cross-sectional side view of the steering-wire locking mechanism 300 of FIG. 3A in an unlocked configuration, consistent with various embodiments of the present disclosure. When an actuation force, $F_1$, is applied upward, upward wedge 301 is pulled upward correspondingly extending spring $305_2$ relative to downward wedge 302. This upward motion of the upward wedge allows the upper portions of side wedges 303 and 304 to collapse inward via spring force from spring $305_1$. Simultaneously, the force exerted on downward wedge 302 by spring $305_2$ causes lower portions of the side wedges to maintain contact with the wall 310. Resulting dislocations of wedges in response to the actuation force causes high frictional coefficient regions $306_{1-2}$ to lose contact with wall 310, allowing for improved sliding characteristics between the mechanism 300 and the wall 310.

The dislocations of wedges comprising the locking mechanism 300, as shown in FIG. 3B, results in a reduced friction state between an outer surface of the side wedges 303 and 304 and inner wall 310. The locking mechanism may then extend longitudinally, relative to the wall, with minimal frictional resistance.

When a force, $F_1$, is released, spring $305_2$ pulls the upward wedge 301 downward. The upward wedge laterally pushes the side wedges 303 and 304 apart, bracing the locking mechanism 300 in place against the wall 310 (as shown in FIG. 3A).

While the functionality of the locking mechanism of FIGS. 3A-B has been described with reference to an upward actuation force exerted, the mechanism would similarly function in response to a downward actuation force. As a result, the present embodiment is capable of being a bi-directional locking mechanism and may moreover be used with a steering wire coupled to either end of the mechanism, or with complimentary steering wires coupled to either end of the mechanism. In operation, the tensioning of one of the complimentary steering wires, for a bi-directionally deflectable intravascular catheter, would reduce the tension on another of the steering wires facilitating the desired deflection of a distal portion of a catheter shaft.

While the present embodiment is directed to a locking mechanism with distinct frictional coefficient regions, a skilled artisan would appreciate that various modifications are readily apparent for achieving the same result as the present embodiment—that is, desirable frictional characteristics for both locked and unlocked configurations of the locking mechanism 300. For example, the outer wall of the side wedges may utilize a continuously varying amount of surface texturing to achieve the desired frictional coefficients along the side wedges. Specifically, the top and bottom portions of the side wedges' side wall may have relatively smooth surfaces with the amount of surface texturing increasing toward an intermediary portion between the top and bottom portions. In yet other embodiments, the outer diameter of the side wedges may have one or more inserts which facilitate the insertion of various materials and/or surface texturing to achieve a desired frictional coefficient.

By virtue of the various frictional coefficient regions along a side wall (or outer diameter) of the side wedges, both high and low friction states may be achieved by the locking mechanism. Accordingly, a high friction region of the side wedges may be used to hold the locking mechanism in place relative to the shaft wall, and a low friction region may allow for reduced force steering inputs by a clinician.

Upon discontinuance of an actuation force of locking mechanism 300, the mechanism returns to a static, locked configuration as shown and discussed in reference to FIG. 3A above.

Figure 3C:
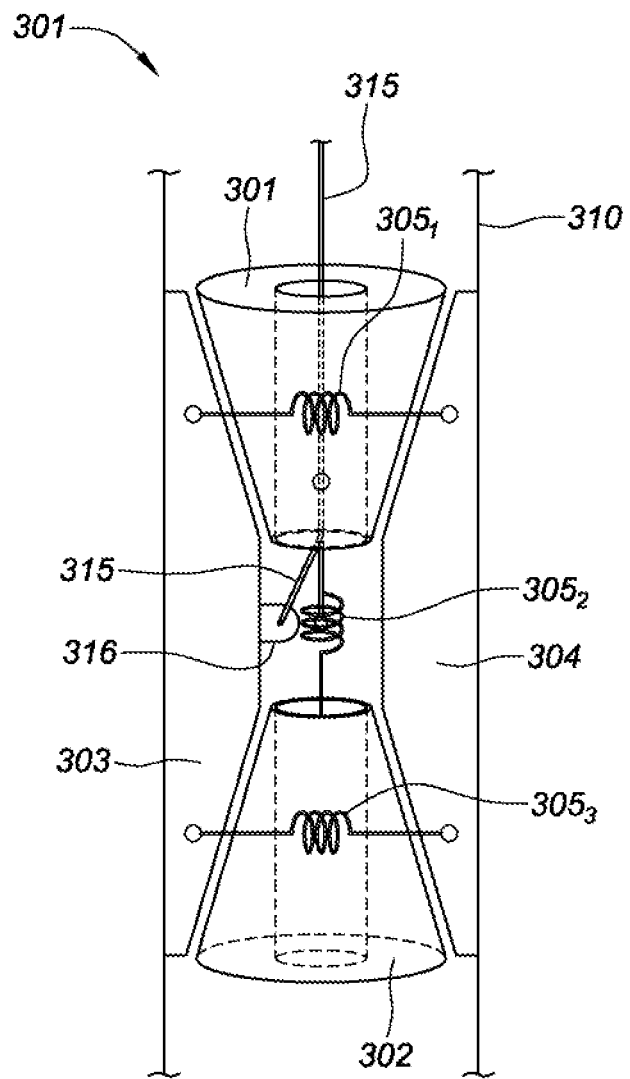
FIG. 3C is a partial cross-sectional, isometric side view of the steering-wire locking mechanism of FIG. 3A (with hidden lines shown for additional detail), consistent with various embodiments of the present disclosure.

While FIGS. 3A-3C are presented as three-dimensional structures, specifically cylindrical structures (shown in cross-section), a skilled artisan will appreciate that such a locking mechanism may also be implemented as a 2-dimensional structure.

FIG. 3C is a partial cross-sectional side view of the steering-wire locking mechanism 300 of FIG. 3A (with hidden lines shown for additional detail). As shown in FIG. 3C, a steering wire (or pull wire) 315 is coupled to at least one of the side wedges 303/304 via a mounting bracket 316. Accordingly, when the locking mechanism 300 is in a locked configuration, the side wedges restrict motion of the steering wire 315.

Some example benefits of a quad-wedge locking mechanism 300 (as disclosed in reference to FIGS. 3A-C) include automatic locking of the locking mechanism absent a steering input by the clinician. That is, no positive action need be taken by the clinician to maintain an input disposition of the distal portion of the catheter shaft. Upward and downward wedges 301/302, in the absence of a steering force on a steering actuator of a catheter handle, drive side wedges 303/304 radially outward—contacting the outer diameter surface of the side wedges with shaft wall 310. Contact between the side wedges and shaft wall 310 lock the locking mechanism 300 in place against the shaft wall 310. The dual-wedge configuration, as discussed in more detail below, also benefits from such automatic locking functionality absent a steering input from a clinician. The side-wedges of the quad-wedge configuration may utilize high friction surface(s) on an outer diameter, which contact the shaft wall in a locked configuration, but which are (entirely) removed from contact with the shaft wall when released. This locking mechanism motion allows for desirable, low friction, steering actuation by a clinician. As discussed above, the outer diameter of the side-wedges may also include low-friction regions, on either end of the high friction surface(s), that may contact the wall in an unlocked configuration, but which minimally increase the sliding friction of the locking mechanism 300. As a result, aspects of the present disclosure benefit from desirable frictional characteristics of the locking mechanism in both locked (no steering actuation and increased frictional state of the locking mechanism) and un-locked configurations (steering actuation, and a reduced frictional state of the locking mechanism).

Figure 4A:
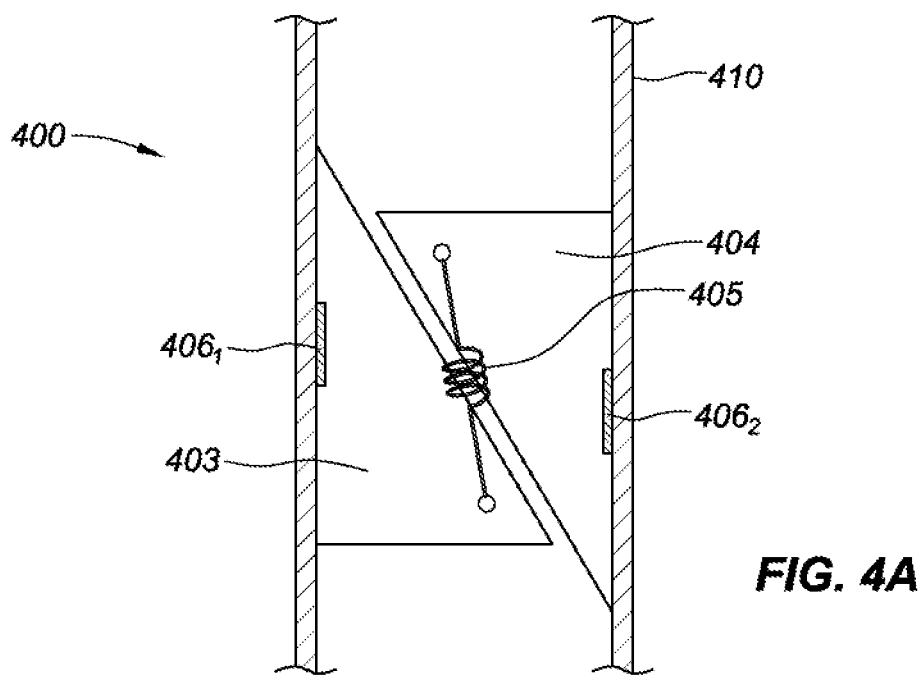
FIG. 4A is a partial, cross-sectional side view of a steering-wire locking mechanism in a locked configuration, consistent with various embodiments of the present disclosure.
Figure 4B:
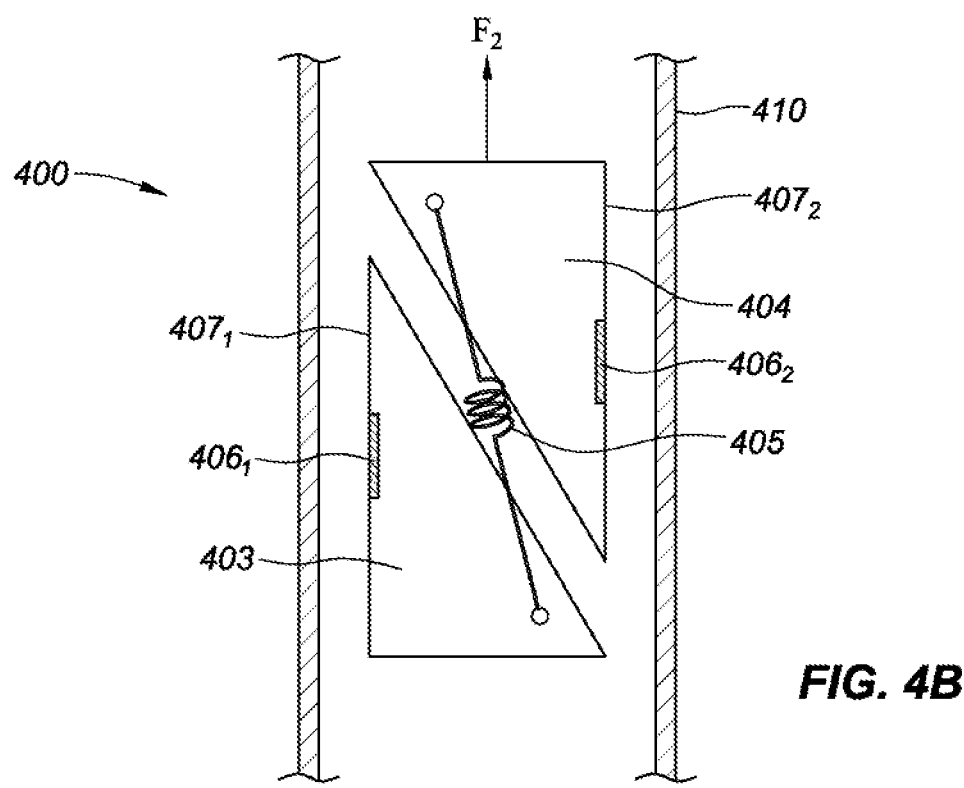
FIG. 4B is a partial, cross-sectional side view of the steering-wire locking mechanism of FIG. 4A in a locked configuration, consistent with various embodiments of the present disclosure.

FIG. 4A is a partial, cross-sectional side view of a steering wire locking mechanism 400 in a locked configuration, and FIG. 4B is a partial, cross-sectional side view of the steering-wire locking mechanism of FIG. 4A in an un-locked configuration, consistent with various embodiments of the present disclosure. With a dual-wedge configuration, as shown in FIGS. 4A-B, one or both of wedges 403/404 are coupled to an actuated steering mechanism which may deflect a distal portion of a catheter via one or more steering wires placed into tension. When an upward force $F_2$, for example, is applied to the upward wedge 404, the wedges pull apart and unlock from wall 410 (as shown in FIG. 4B), allowing the mechanism to slide with reduced friction. When no steering actuation is present, spring 405 pulls the wedges back together. The complimentary shape of the wedges causes the wedges to extend radially outward as they are drawn together, thereby locking the mechanism 400 against wall 410.

As shown FIGS. 4A-B, outer surfaces $407_{1-2}$ may include one or more high-friction regions $406_{1-2}$ which may be formed entirely of a high-friction material, and/or include a combination of surface finishes. As shown in reference to FIG. 3B, portions of the wedges 403/404 may still contact wall 410 when actuated into an unlocked configuration. Accordingly, some specific embodiments may include low-frictional coefficient regions along a length of the outer surfaces $407_{1-2}$, except for the defined one or more high-friction regions $406_{1-2}$. These high-friction regions $406_{1-2}$ may be placed at locations along the length of the outer surface which are less likely to contact the wall 410 in an unlocked configuration of the locking mechanism 400 (e.g., an intermediary portion of the outer surface).

As shown in FIG. 4A, when no force is applied to the locking mechanism 400, spring 405 pulls the two wedges 403/404 together and the wedges push each other radially outward and into contact with wall 410. The high-friction regions $406_{1-2}$ of the outer surfaces $407_{1-2}$ engage with the wall and lock the mechanism in place (and thereby steering wires coupled thereto).

When an upward force, $F_2$, is applied to the upward wedge 404, the wedges are pulled apart and extend radially inward. The high-friction regions $406_{1-2}$ no longer contact wall 410, as shown in FIG. 4B. The locking mechanism 400 is thereby unlocked relative to wall 410 and the locking mechanism may move freely in the direction of force $F_2$. The locking mechanism 400 responds similarly to the application of a downward force on the downward wedge 403. The wedges 403/404 disengage from the shaft wall 410 allowing for longitudinal motion of the locking mechanism in the direction of the force applied.

Some example benefits of the dual-wedge locking mechanism 400 of FIGS. 4A-B include no action by a clinician to lock the one or more steering wires in the absence of a steering actuation. The upward and downward wedges 403/404, in the absence of a steering force on the steering actuator, push each other radially outward locking the locking mechanism 400 in place against wall 410. As the wedges of the dual-wedge configuration utilize a combination of high and low-friction surface regions, locked and unlocked configurations may be achieved with the shaft wall and wedges remaining at least partially in contact with one another. Specifically, such embodiments facilitate desirable, low-friction, steering actuation by the clinician and a high-friction locked configuration of the locking mechanism 400 absent a clinician steering input.

While the functionality of the steering-wire locking mechanism 400 of FIGS. 4A-B has been described with reference to an upward force, $F_2$, the mechanism would similarly function in response to a downward force. As a result, the present embodiment is capable of being a bi-directional locking mechanism and may moreover be used with a steering wire coupled to either end of the mechanism, or with complimentary steering wires coupled to either end of the wedges. In a complimentary steering wire embodiment, the tensioning of one of the steering wires, for a bi-directionally deflectable intravascular catheter, would reduce the tension on the other steering wire facilitating the desired deflection of a distal portion of catheter shaft without the non-actuated wire resisting the desired deflection.

While FIGS. 4A-4B are presented as three-dimensional structures, specifically cylindrical structures (shown in cross-section), a skilled artisan will appreciate that such a structure may also be implemented as a 2-dimensional structure.

Specific/Experimental Embodiment

FIGS. 5-10B are directed to a specific/experimental locking mechanism embodiment, consistent with various aspects of the present disclosure.

Figure 5:
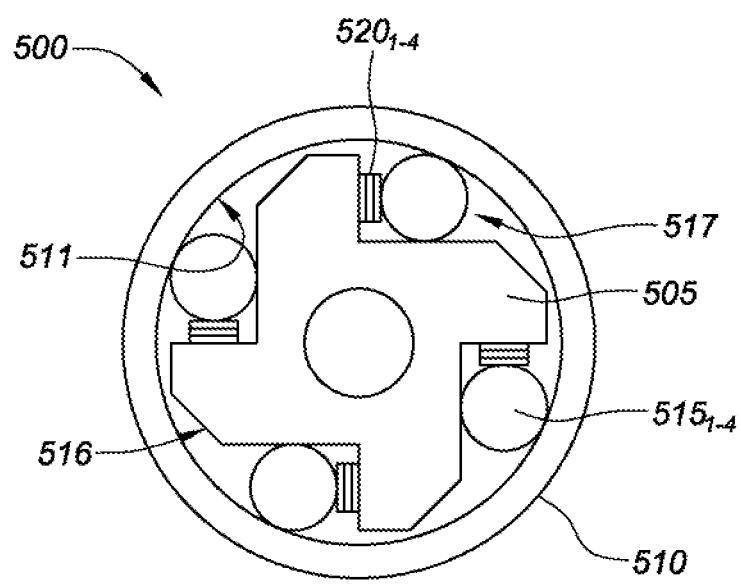
FIG. 5 is a top view of a unidirectional bearing of a steering-wire locking mechanism, consistent with various embodiments of the present disclosure.

FIG. 5 is a top view of a unidirectional bearing 500 of a steering-wire locking mechanism, consistent with various embodiments of the present disclosure. As shown in FIG. 5, the unidirectional bearing 500 includes an inner race 505, outer race 510, rollers $515_{1-4}$ and compression springs $520_{1-4}$. The outer race 510 is comprised of a cylindrical shell with a defined inner cylindrical surface 511, while the inner race 505 has a regularly patterned but irregularly shaped outer surface 516. When assembled, the inner and outer races form convergent race channels 517 along a circumferential direction (clockwise or counterclockwise). The rollers and compression springs are inserted into the individual convergent race channels 517. The rollers 515 may be short cylinders or spherical balls and may comprise various metal, metal alloys and/or one or more polymeric materials. Compression springs 520 may be mounted in channels 517 of the inner race 505, and positioned relative to the rollers 515 to facilitate constant contact between the inner cylindrical surface 511 of the outer race 510 and the rollers.

The unidirectional bearing 500 facilitates free unidirectional rotation of the bearing in response to actuation of the bearing in a first rotational direction, and transmits high resistance torque (or power) in response to rotation of the bearing in a second rotational direction. For the unidirectional bearing system 500 illustrated in FIG. 5, either the inner or outer race may be the driving component. For example, when the inner race is used as the driving component, the outer race will be the driven component (and vice versa). The driving component is the one which receives a steering actuation by a clinician and is coupled to a steering wire. When the inner race 505 is used as the driving component for actuating a steering wire and rotates in a clockwise direction, frictional forces imposed on the rollers 515 by the driven component, i.e. outer race 510, cause compression on the spring 510 which gives the rollers additional clearance to roll within the convergent race channels 517. As a result, the inner race 505 may freely rotate in the clockwise direction, allowing for actuating the steering wire. When the actuation force is released, the inner race 505 would have a tendency to rotate in a counterclockwise direction due to the pull force from the activated steering wire. The driven component, the outer race 510, would tend to impose frictional forces on the rollers that would push rollers 515 toward a surface of the inner race, where compression of the springs 520 may not facilitate additional clearance for the rollers. As a result, the interacting surfaces between the inner race, outer race, and rollers exhibit high-friction characteristics, resisting and/or preventing the counterclockwise rotation of the inner race relative to the outer race.

In the unidirectional bearing 500 of FIG. 5, if the outer race is physically fixed relative to a rotatable inner race, the counterclockwise rotation for the inner race is not possible (i.e. self-locking) due to the "squeezing" action of rollers 515 within the convergent race channels 517 between the inner and outer races. Similarly, the outer race may be used as the driving component and coupled to a steering wire for deflecting the distal portion of a catheter shaft, but the direction for free and locked rotations reverse.

In accordance with the above discussion, a skilled artisan will understand that the operational principles of unidirectional bearings may be utilized to design various self-locking mechanisms for bidirectional lateral actuators of deflectable intravascular catheters.

Figure 6A:
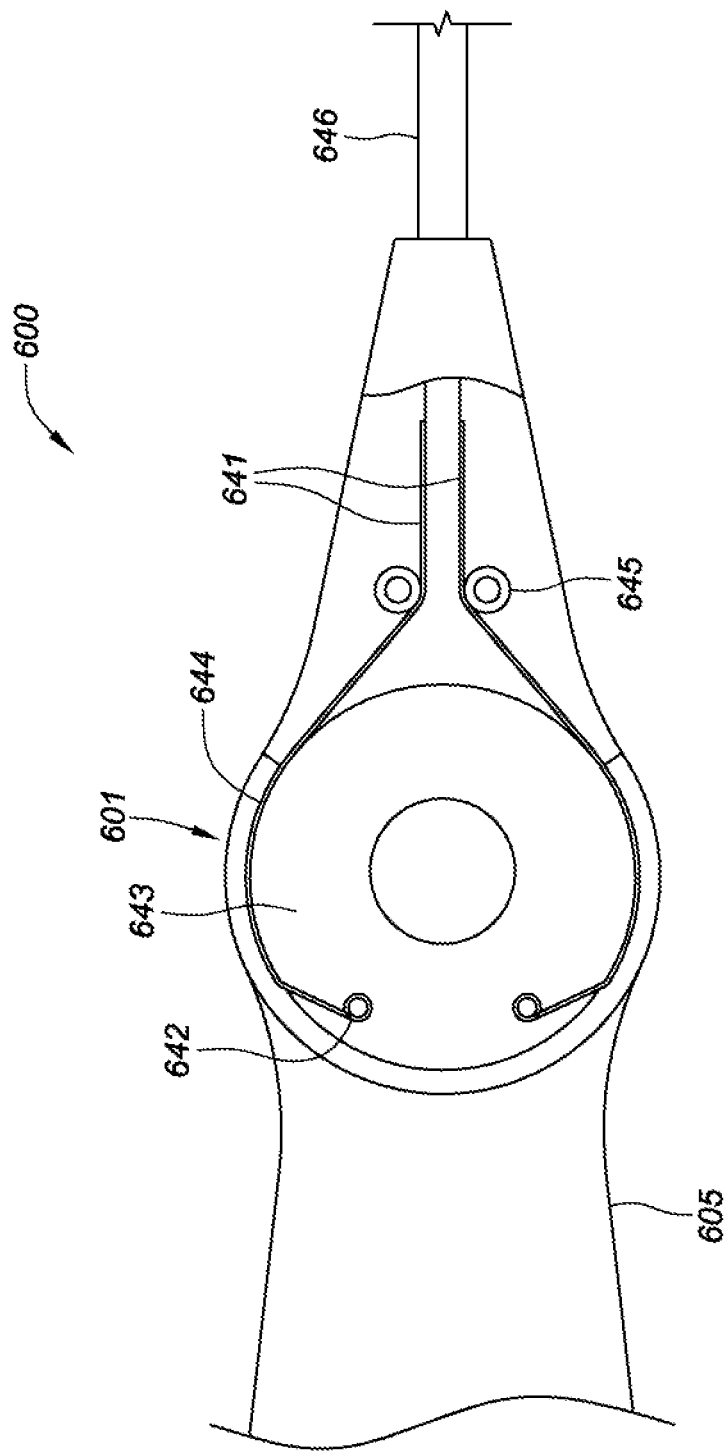
FIG. 6A is a partial, cross-sectional, top view of a catheter handle including a steering-wire locking mechanism, consistent with various embodiments of the present disclosure.
Figure 6B:
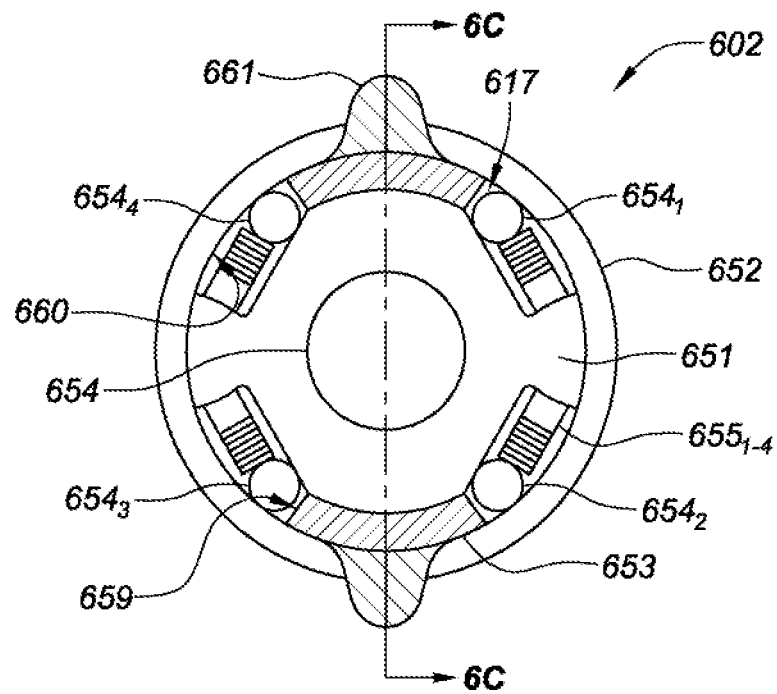
FIG. 6B is a top view of a unidirectional bearing of the catheter handle of FIG. 6A, consistent with various embodiments of the present disclosure.
Figure 6C:
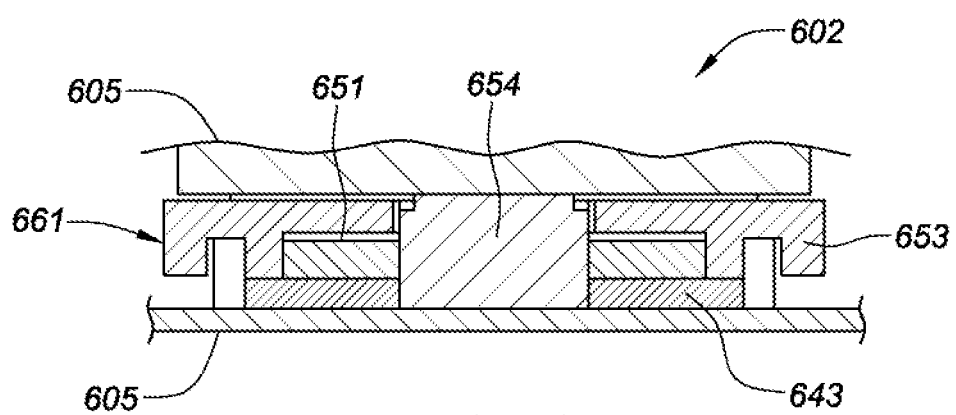
FIG. 6C is a cross-sectional front view of the unidirectional bearing of FIG. 6B, consistent with various embodiments of the present disclosure.

FIG. 6A is a partial, cross-sectional, top view of a catheter handle 600 including a steering-wire locking mechanism, FIG. 6B is a top view of a unidirectional bearing 602 of the catheter handle of FIG. 6A, and FIG. 6C is a cross-sectional front view of the unidirectional bearing 602 of FIG. 6B, consistent with various embodiments of the present disclosure.

As shown in FIG. 6A, catheter handle 600 includes a lateral actuator 601 which receives clinician steering inputs and transforms the inputs into linear actuations on steering wires 641. The proximal ends of the steering wires are coupled to anchors 642 and are distally routed about an outer wall 644 of a receptacle disc 643. The actuating disc 643 is rotatably coupled to an actuator 661 of the catheter handle (as shown in FIG. 6B). In response to a rotation of the actuating disc 643, the relative radial locations of the anchors about a center point of the actuating disc changes. The radial motion of the anchors and the outer wall cause tension in one of the steering wires 641 and a proportional release of tension in the other steering wire. The steering wires extend distally from the anchors, along the outer wall of the actuating disc, are relayed by re-directing rollers 645, and extend distally through catheter shaft 646 before arriving and being coupled to a pull-ring in proximity to a distal tip of the catheter shaft.

To integrate a unidirectional bearing 602 (as shown in FIG. 6B) with a lateral actuator 601 of a catheter handle 600 (as shown in FIG. 6A), outer race 652 (which is fixed in the present embodiment) may be coupled to catheter handle housing 605, while inner race 651 (or deflecting race) is allowed to freely rotate about a housing pivot 654 in a selected clockwise (or counterclockwise) direction. The inner race is coupled to a receptacle disc 643 of the lateral actuator 601 (i.e., a wrapping rope mechanism). In yet other embodiments, the lateral actuator 601 may be one of various, other pull-wire mechanisms (i.e. a sliding linkage, or a rack-gear mechanism, or a wrapping flexible cord mechanism) that transform lateral actuations of the inner race 651 into linear displacement of one or more steering wires (or pull wires) 641 fixed to a distal pull ring of the deflectable catheter shaft 646.

As shown in FIG. 6B, inner race 651 is the actuating race with one or two steering wires coupled to it. Inner race 651 can rotate about pivot 654 of handle housing 605, while the outer race 652 may be integrated into the handle housing, and accordingly fixed in position. When assembled, the inner race and the outer race form convergent race channels 617 with two pairs of rotational orientations: clockwise and counterclockwise. The convergent race channels are circumferentially aligned with the body pivot. Within the convergent channels, individual rollers $654_{1-4}$ (cylindrical or spherical) and compression springs $655_{1-4}$ are arranged so that the rollers maintain contact with an inner cylindrical surface 660 of the outer race 652. To affect free rotation of the inner race, an actuating disc 653 has an actuating lever 661 integrated thereto. In operation, unidirectional bearing 602 has three operating states: actuating, self-locked and unlocked states which will be described in more detail below.

In response to an actuation of lever 661 (by a clinician) in a clockwise direction, rollers $654_{1-3}$, which are contained in convergent channels 617 and oriented in the counterclockwise direction, tend to lock or prevent inner race 651 from the clockwise rotation. To unlock the inner race, an actuator disc 653 (which is integrated with the lever) is clockwise rotated to make contact with rollers $654_{1-3}$ (via slant surface 659) and push them towards the opposite end of the convergent race channels 617. Simultaneously, other rollers $654_{2-4}$, which are contained in the convergent channels and oriented in the clockwise direction, automatically free the inner race 651 for clockwise rotation of the inner race driven by the actuator disc 653. This further activates clockwise rotation of receptacle disc 643 coupled to the inner race (see FIGS. 6A and 6C), which transforms the actuated rotational motion of the inner race to the linear pulling motion for one active steering wire and the linear releasing motion for the other passive pull-wire, leading to the lateral deflection of a distal portion of catheter shaft 646. When a clinician's input on actuating lever 661 is released, the active steering wire in tension may exert a counterclockwise torque on the inner race 651. However, such counterclockwise rotation of the inner race (absent clinician's actuation torque) is automatically prevented by the rollers $654_{2-4}$ which are oriented along their respective convergent race channels in the clockwise directions, because of the static frictional forces exerted on the inner race by these rollers. This counter-clockwise rotation on the inner race tends to sandwich the rollers $654_{2-4}$ between the inner cylindrical surface 660 and inner race 651. As a result, unidirectional bearing 602 self-locks, after a clinician has completed the deflection of catheter shaft into a deflected configuration, and maintains the deflected state (unless a follow-on clinician actuation occurs on actuating lever 661).

It is noted that rollers 654 may be placed into two distinct convergent channels 617, based on an orientation of the rollers (e.g., counterclockwise or clockwise orientation). The distinct convergent channels 617 may be positioned symmetrically about housing pivot 654. Accordingly, counter-clockwise actuation on actuating lever 661 may cause a lateral deflection of the distal portion of catheter shaft 646, which is self-locking upon the release of the actuating lever. Actuation of the actuating lever by the clinician to adjust the extent of the catheter shaft deflection frees or unlocks the self-locked rollers 654 during the transient deflection period. Therefore, for the deflection of catheter shaft by unlocking unidirectional bearing 602, a minimal actuation torque is merely required to exceed the frictional resistance of the system (e.g., static and kinetic frictional forces between the rollers, and inner and outer races (which are reversibly low).

As further illustrated in FIG. 6C, receptacle disc 643 may be integrated with inner race 651. The receptacle disc transmits the rotational motion of actuating lever 661 to the steering-wire mechanism (also referred to as lateral actuator 601), which transforms the rotational motion to a linear motion of steering wires (pull wires) 641, which are coupled at distal ends to pull rings near a distal tip portion of deflectable catheter shaft 646 (as shown in FIG. 6A).

The races and rollers, in the various embodiments disclosed herein, may comprise materials including one or more of the following: non-lubricious thermoplastics and thermoplastic elastomers. More specifically, the races and rollers may comprise materials including one or more of the following: polycarbonate, acrylonitrile butadiene styrene, polysulfones, polyoxymethylene homopolymer and copolymers, polyamides, polyesters, and polyimides. Metallic materials may also be utilized.

FIGS. 7A-9B illustrate some example structural designs for the essential components of a roller type, self-locking mechanism or unidirectional bearing. Specifically, the self-locking mechanism, as disclosed herein, features convergent race channels with competing rotational orientations. The self-locking mechanism includes an actuating race (or inner race) assembly 700 as shown in FIGS. 7A-B, a fixed race (or outer race) 800 as shown in FIGS. 8A-B, and actuating lever 900 as shown in FIGS. 9A-B.

FIG. 7A is a cross-sectional front view of an inner race assembly 700 of a steering-wire locking mechanism and FIG. 7B is a top view of the inner race of FIG. 7A, consistent with various embodiments of the present disclosure. As shown in FIGS. 7A-B, the inner race assembly includes an inner race 701 and a receptacle disc 702 which are coupled to one another. As discussed above, the receptacle disc 702 interfaces with a pull-wire mechanism of the catheter handle. The inner race 701 is a boss that extends up from a top surface of the receptacle disc 702. An outer perimeter surface of the inner race is a roller surface 703 on which rollers of the locking mechanism travel. Inner surfaces 704/705 of both the inner race and receptacle disc may be coupled to an outer diameter of housing pivot 654 (as shown in FIG. 6C). As shown in FIG. 7B, inner race assembly 700 includes convergent race channels $717_{1-2}$ which are positioned symmetrically about a central axis when assembled with the actuating disc, each channel is divided into two symmetric channels. Two, opposing rollers are placed in each of the convergent race channels, and each of the rollers is paired with a spring. Each of the springs are assembled on respective spring bosses $718_{1-4}$.

FIG. 8A is a cross-sectional front view of an outer race assembly 800 of a steering-wire locking mechanism, and FIG. 8B is a top view of the outer race assembly of FIG. 8A, consistent with various embodiments of the present disclosure. The outer race assembly, in the present embodiment, includes both an outer race 802 and a housing pivot 801 which are co-axial with one another and physically fixed with the handle housing 605 (FIG. 6C). As discussed above, receptacle disc 702 and inner race 701 (as shown in FIG. 6C) are rotatably coupled to an outer surface 803 of the body pivot 801. The inner race and outer race 802 circumferentially contain the rollers within convergent race channels of the inner race assembly.

FIG. 9A is a cross-sectional front view of an actuating disc 900 of a steering-wire locking mechanism, and FIG. 9B is a top view of the actuating disc of FIG. 9A, consistent with various embodiments of the present disclosure. The actuating disc includes actuating levers $901_{1-2}$ which transmit an actuating force from a clinician to an inner race of the steering-wire locking mechanism. Specifically, the rotational actuation of the actuating disc is transmitted to the inner race via roller contacting surfaces $902_{1-4}$. The roller contacting surfaces make direct contacts with two "locked" rollers in response to a clockwise (or counterclockwise) rotation of the actuating disc and exert the torque through the roller and springs to the inner race.

Figure 10A:
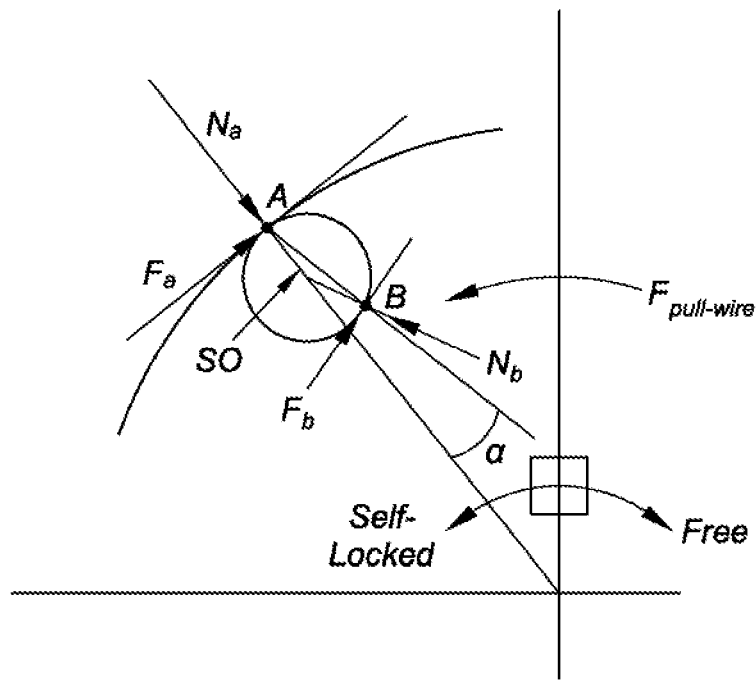
FIG. 10A is a force analysis diagram of a steering-wire locking mechanism, consistent with various embodiments of the present disclosure.
Figure 10B:
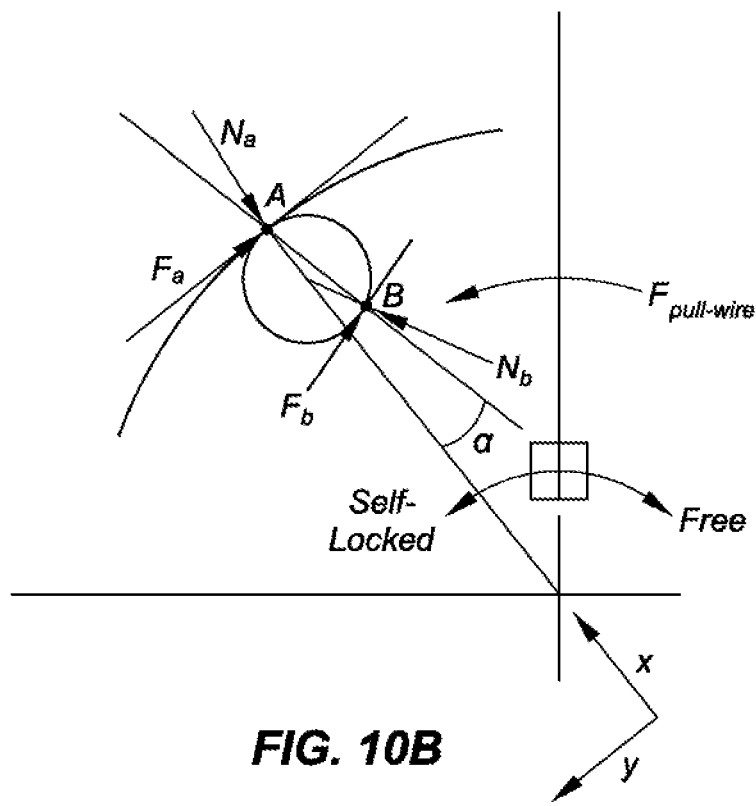
FIG. 10B is a force analysis diagram of a steering-wire locking mechanism, consistent with various embodiments of the present disclosure.

FIGS. 10A-B are force analysis diagrams of a steering-wire locking mechanism, consistent with various embodiments of the present disclosure. The force analysis diagrams of FIGS. 10A-B show the forces imposed on a steering-wire locking mechanism, consistent with the present disclosure, after the catheter shaft is deflected in the clockwise direction and the actuating lever is released. The counterclockwise torque ($M_{wire}$) transformed from the active steering wire to the mechanism would tend to return the shaft from a deflected configuration back to a neutral state. Here, $S_0$ is the initial compression force on the roller imposed by the spring at the system's neutral, assembled state; $N_a$ and $F_a$ are normal force and static frictional force, respectively, imposed on the rollers by the fixed race (i.e. outer race). $N_b$ and $F_b$ are the normal force and static frictional force imposed on the rollers by the actuating race (i.e. inner race). In regard to FIG. 10A, initial compression force $S_0$ pushes the roller towards the narrowing portion of the convergent race channel, which is favorable to the formation of the self-lock state of the roller. To derive the self-locking condition for the roller under the counterclockwise torque ($M_{wire}$) arising from the active steering wire, we consider the worst-case scenario—where the initial compression force on the self-locking roller $S_0$ is zero (which is shown in FIG. 10B). The equilibrium conditions for the locking state of a roller within the clockwise convergent race channel are:

$\Sigma M_o^i = 0: F_a = F_b$ $\Sigma F_{x=\overline{OA}}^i = 0: -N_a + N_b \cos 2\alpha + F_b \sin 2\alpha = 0$ $\Sigma F_{y=perpendicular\ to\ \overline{OA}}^i = 0: -F_a + N_b \sin 2\alpha = 0$ From the above, the following equation may be derived:

$$F_a = \frac{\sin 2\alpha}{1 + \cos 2\alpha} N_a = N_a \tan \alpha$$

To achieve the self-locking state for the roller, it is understood that $F_a < \mu_s N_a$. $\mu_s$ is the coefficient of static friction between the material pairs of the roller and outer race. Therefore, from the above expression, the following self-locking condition for the locking mechanism is:

$\alpha < \tan^{-1} \mu_s$

Here, the angle α is a grip or convergence angle for the race channels. That is, the angle between a first normal plane extending from an inner surface of the outer race, and a second normal plane extending from a slant surface 659 (as shown in FIG. 6B). By properly selecting the diameters and material combinations for the rollers and the outer race, the above self-locking conditions may be met along with the proper geometric designs for the inner race.

While aspects of the present disclosure have been presented as being readily applicable to ablation catheters, aspects of the present disclosure are also readily applied to various other electrophysiology catheters (e.g., mapping catheters, electrophysiology basket catheters, ablation balloon catheters, etc.). Further, aspects of the present disclosure have been discussed including diagnosis and treatment of cardiac arrhythmias (e.g., atrial fibrillation); however, the present disclosure is readily applicable to the diagnosis and treatment of a number of different ailments, for example, Brugada syndrome.

Although several embodiments have been described above with a certain degree of particularity, those skilled in the art could make numerous alterations to the disclosed embodiments without departing from the spirit of the present disclosure. It is intended that all matter contained in the above description or shown in the accompanying drawings shall be interpreted as illustrative only and not limiting. Changes in detail or structure may be made without departing from the present teachings. The foregoing description and following claims are intended to cover all such modifications and variations.

Various embodiments are described herein of various apparatuses, systems, and methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," "an embodiment," or the like, means that a particular feature, structure, or characteristic described in connection with the embodiment is included in at least one embodiment. Thus, appearances of the phrases "in various embodiments," "in some embodiments," "in one embodiment," "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The invention claimed is:

1. A steering-wire locking system for deflecting a distal portion of a catheter shaft comprising:
   an outer race;
   an inner race co-axial with the outer race, the outer race circumferentially extending around the inner race, the inner race including a plurality of channels that extend into an outer perimeter of the inner race, the plurality of channels configured and arranged to each house a pair of compression springs and rollers; a plurality of rollers configured and arranged to rotate within the plurality of channels confined by an outer surface of the inner race and an inner surface of the outer race; a plurality of compression springs configured and arranged to position the rollers in one of two positions within the plurality of channels.

2. The steering-wire locking system of claim 1, wherein the compression springs are further configured and arranged
   in response to a clockwise rotation of the inner race, to position a first roller of the plurality of rollers in a first position, and a second roller of the plurality of rollers in a second position, and
   in response to a counter-clockwise rotation of the inner race, to position the first roller of the plurality of rollers in the second position, and the second roller of the plurality of rollers in the first position.

3. The steering-wire locking system of claim 2, wherein, at the first position, the first roller is in contact with a distal end of the paired spring, within one of the channels, and where the paired spring is fully extended and the first roller exhibits a limited frictional coefficient on the inner and outer races; and at the second position, the first roller is in contact with the distal end of the paired spring, and where the paired spring is at least partially compressed and the first roller exhibits an enhanced frictional coefficient on the inner and outer races.

4. The steering-wire locking system of claim 1, wherein the plurality of channels are convergent race channels that are configured and arranged to house a pair of opposing rollers and compression springs.

5. The steering-wire locking system of claim 1, further including an actuating lever which is coupled to the inner race and which is configured and arranged to receive a user actuation and transmit the actuation to the inner race.

6. The steering-wire locking system of claim 1, wherein the inner race is symmetrical about a rotational axis of the steering-wire locking system.

7. The steering-wire locking system of claim 1, wherein the plurality of channels of the inner race include a variable outer diameter, the variable outer diameter of the channels configured and arranged to affect frictional forces between the inner race, outer race, and roller, based upon the relative position of the roller with the channel.

8. The steering-wire locking system of claim 1, wherein an outer diameter of the plurality of channels is formed by an inner diameter of the outer race, and the plurality of channels are convergent race channels alternately oriented, about a circumference of the steering-wire locking system, in clockwise and counterclockwise directions.

9. The steering-wire locking system of claim 8, wherein the alternately oriented convergent race channels include
clockwise oriented convergent race channels including a first pair of compression spring and roller, the roller of the first pair is located clockwise of the spring in the first pair, and
counter-clockwise oriented convergent race channels including a second pair of compression spring and roller, the roller of the second pair is located counter-clockwise of the spring in the second pair.

10. The steering-wire locking system of claim 1, wherein the plurality of channels include radially extending surfaces, the plurality of springs are coupled to the one or more radially extending surfaces, the plurality of springs further configured and arranged to impose compression forces on the rollers which guide the rollers toward a convergent portion of the plurality of channels.

11. The steering-wire locking system of claim 1, wherein the plurality of springs are configured and arranged to maintain constant contact between the rollers and the inner and outer races.

12. The steering-wire locking system of claim 1, further including an actuating lever with a plurality of protruding fingers which extend between adjacent channels of the plurality of channels.

13. The steering-wire locking system of claim 1, wherein the plurality of channels include a slanted surface configured and arranged to contact the respective rollers in response to actuation of the steering-wire locking system, and wherein an angle $\alpha$ between a first plane normal to the inner surface of the outer race and a second plane normal to the slanted surface of the inner race is controlled by:

$$\alpha < \tan^{-1} \mu_s,$$

where $\mu_s$ is the static coefficient of friction of the roller against the outer race.

14. The steering-wire locking system of claim 1, wherein the inner and outer races and the plurality of rollers comprise materials including one or more of the following: non-lubricious thermoplastics and thermoplastic elastomers.

15. The steering-wire locking system of claim 1, wherein the inner and outer races and the plurality of rollers comprise materials including one or more of the following materials: polycarbonate, acrylonitrile butadiene styrene, polysulfones, and polyimides.

16. The steering-wire locking system of claim 1, wherein the outer race is fixed to a catheter handle housing, and the inner race is configured and arranged to bi-directionally rotate relative to the outer race.

17. The steering-wire locking system of claim 1, further including an actuating lever and a receptacle disc both coupled to the inner race, the receptacle disc configured and arranged to transmit a radial motion from the inner race to a pull-wire mechanism.

18. The steering-wire locking system of claim 1, wherein the inner race is fixed to a catheter handle housing, and the outer race is configured and arranged to unidirectionally or bi-directionally rotate about the inner race.

19. The steering-wire locking system of claim 18, further including a receptacle disc coupled to the outer race, the receptacle disc configured and arranged to transmit a radial motion from the outer race to a pull-wire mechanism.

* * * * *